United States Patent
Darimont et al.

(10) Patent No.: US 7,294,509 B2
(45) Date of Patent: Nov. 13, 2007

(54) PRE-ADIPOSE CELL LINES

(75) Inventors: Christian Darimont, Lausanne (CH); Katherine Mace, Lutry (CH); Andrea Pfeifer, St-Légier (CH)

(73) Assignee: Nestec S.A., Vevey (CH)

( * ) Notice: Subject to any disclaimer, the term of this patent is extended or adjusted under 35 U.S.C. 154(b) by 184 days.

(21) Appl. No.: 10/348,480

(22) Filed: Jan. 21, 2003

(65) Prior Publication Data

US 2003/0175957 A1    Sep. 18, 2003

Related U.S. Application Data

(63) Continuation-in-part of application No. PCT/EP01/08165, filed on Jul. 13, 2001.

(30) Foreign Application Priority Data

Jul. 18, 2000   (EP)   ................... 00115489

(51) Int. Cl.
*C12N 5/00*   (2006.01)
*C12N 5/02*   (2006.01)
*C12N 15/00*  (2006.01)
*C12N 15/08*  (2006.01)
*C12N 15/87*  (2006.01)
*C12P 21/06*  (2006.01)

(52) U.S. Cl. ................. 435/325; 435/69.1; 435/320.1; 435/366; 435/377; 435/455; 435/467

(58) Field of Classification Search ............... 435/69.1, 435/320.1, 325, 455, 375, 377, 366
See application file for complete search history.

(56) References Cited

U.S. PATENT DOCUMENTS

| 5,827,740 A | 10/1998 | Pittenger ................... 435/372 |
| 5,830,682 A | 11/1998 | Moore ........................ 435/29 |
| 6,071,747 A | 6/2000 | Strosberg et al. ........... 435/467 |

OTHER PUBLICATIONS

Christian et al Biochimie. 85(12):1231-3, 2003.*
Sugihara H., et al.: "Primary cultures of unilocular fat cells: Characteristics of growth in vitro and changes in differentiation properties." vol. 31, 1996, pp. 42-49, XP000990058. Department of Pathology, Saga Medical School, Saga 840-01, Japan.
Kolarova P., et al.: "Conditional immortalization of white adipocytes using SV40 large T-antigen from the transgenic mouse." European Journal of Cell Biology, vol. 74, No. suppl. 47, 1997, p. 87. XP000990293.
Thomas M., et al.: "Formation of functional tissue from transplanted adrenocortical cells expressing telomerase reverse transcriptase." Nature Biotechnology, vol. 18, No. 1, Jan. 2000-2001, pp. 39-42, XP002185530.

* cited by examiner

*Primary Examiner*—Sumesh Kaushal
(74) *Attorney, Agent, or Firm*—Bell, Boyd & Lloyd LLP

(57) ABSTRACT

This invention relates to new immortalized human pre-adipose cell lines capable of differentiating into adipose cells and methods of obtaining the immortalized cells. In particular, the present invention pertains to immortalized pre-adipocyte cell lines derived from white adipose tissue and methods of producing the cell lines. The immortalized pre-adipocyte cells are capable of maturing into immortalized white adipose cells useful in developing drugs, food ingredients and supplements against obesity, diabetes and cardiovascular diseases.

12 Claims, 11 Drawing Sheets

Passage:     19   20   21
PDs:         75   76   80

PPARγ

C/EBPα

LPL aP2

A

| Oleate | - | - | - | + |
| BRL49653 | - | - | + | + |
| Dex | + | + | + | + |

B

Dex + BRL49653

Dex + BRL49653 + Oleate

A

Dex + BRL49653

B

Incubation time (day)

PRE-ADIPOSE CELL LINES

CROSS-REFERENCE TO RELATED APPLICATIONS

This application is a continuation-in-part of International application PCT/EP01/08165 filed Jul. 13, 2001 (WO 02/06450 A1 01/24/2002).

BACKGROUND ART

This invention relates to human pre-adipose cell lines capable to differentiate into adipose cells. In particular, the present invention pertains to pre-adipose cell lines derived from white adipose tissue and their use in developing drugs, food ingredients and supplements against obesity, diabetes and cardio-vascular diseases.

Obesity has been declared a public health hazard by the National Institutes of Health. Obesity may be defined as the presence of excess adipose tissue which affects about 30 to 50% of the North American population and a substantial percentage of the population worldwide. The effects of obesity, e.g. non-insulin dependent diabetes, coronary artery disease, and hypertension, are estimated to have resulted in $45.8 billion in direct costs and an additional $23 billion in indirect costs from, e.g., missed work.

It is held that excessive ingestion of fat and carbohydrate induces obesity and hyperlipidemia and even develops hypertension and arteriosclerosis ultimately. The desirability of repressing the absorption of fat and carbohydrate and diminishing the accumulation of fat has, therefore, been finding enthusiastic recognition. Infants, on exposure to excessive caloric intake, suffer increase of adipocytes and assume the state which may well be called potential obesity. By this reason, it has been reported that the repression of the increase of the number of adipocytes particularly in infants results directly in the prevention of the obesity and the cardiovascular diseases which may well be called complications of obesity in children and consequently in adults.

To combat this evident health problem, both prophylactic and therapeutic approaches are necessary. For prophylactic purposes, it would be useful to be able to predict and measure a person's propensity or susceptibility to obesity. For therapeutic purposes, a means for interfering with the development or differentiation of adipocytes (fat cells) would be of great benefit. None of these desired objectives has been achieved so far, which is mainly due to that little is known about the regulation and control of the development of adipose tissue, e.g. the proliferation and differentiation of adipocytes precursors.

The identification of means or substances, respectively, controlling such proliferation and differentiation is very important for understanding normal adipose tissue development and for designing approaches for controlling abnormal states of adipose tissue development such as obesity.

To determine whether a substance is involved in the physiological regulation of adipose tissue development, investigations may be carried out if adipocytes or precursors thereof are responsive to this factor and ultimately if this factor can efficiently and specifically modulate adipose tissue development in vivo. Appropriate studies could not be performed so far, which fact is mainly due to a lack of suitable tissue or cells derived from human adipose tissue exhibiting properties of normal adipocytes from living tissue and being capable to be cultured for a prolonged period in vitro so as to carry out the experiments.

Fat cells or adipocytes (adipose cells) the main cell population of fat tissue represent a principal storage depot for triglycerides, and are deemed to be endocrine cells. Adipose tissue provides an energy storage reserve for the body in the form of triglycerides and this tissue can release free fatty acids when caloric intake falls below metabolic needs. In response to increased dietary intake, the body will normally automatically increase energy expenditure through activity to maintain an energy balance. Energy can also be released as heat. There are common energy regulation pathways that balance dietary intake with metabolic activity largely mediated through the hypothalamus. It is now also apparent that the adipocytes play an active role in this process and likely produce molecules that serve to feed back and effect regulation of triglyceride metabolism. Furthermore, adipocytes are able to secrete hormones which modulate key functions in peripheral or central organs. The best example being the leptin secreted by adipocytes and regulating energy metabolism and satiety via receptors located in hypothalamus. It would therefore be of great interest to be capable to find and investigate such molecules.

There are essentially two types of adipose tissue, brown and white, which carry out quite different roles in the body. White adipose is designed to store excess caloric intake while brown adipose tissue uses a unique system to syphon off excess calories and use it to generate body heat. However, white adipocytes were shown to express uncoupling proteins involving the control of thermogenesis. Since only white adipose tissue subsists in adult humans, thermogenesis induced by white adipose may increase energy expenditure.

SUMMARY OF THE INVENTION

The present invention is directed to a culture of an immortalized human pre-adipose cell line and methods of preparing the same. The culture of the present invention includes immortalized human pre-adipose cells capable of maturing into a immortalized mature white adipose cells. The mature adipose cells derived from the cell line exhibit metabolic patterns of normal human white adipose cells making them extremely useful for use in research and development programs. Typically, when the immortalized mature cells are cultured on serum-free medium they express at least four normal human white adipose cell markers selected from the group consisting of: lipoprotein lipase; fatty acid synthase; adipocyte fatty acid binding protein; leptin; adipsin; adiponectin; peroxisome proliferator-activated receptors γ; peroxisome proliferator-activated receptors β; CCAAT/enchancer binding protein alpha; and hormone sensitive lipase. Preferably, the immortalized cells express the following normal adipoctye markers lipoprotein lipase; leptin; adiponectin; and peroxisome proliferator-activated receptors γ and more preferably, they also express CCAAT/enhancer binding protein alpha, adipocyte fatty acid binding protein or adipsin.

In a preferred embodiment, the immortalized white adipose cell produced from the pre-adipose cell line has a karypotpe identical to normal white adipocytes.

The present invention also is directed to methods of preparing an immortalized pre-adipose cell line. The methods generally comprises the following steps:
 (a) separating cells from a human adipose tissue;
 (b) de-differentiating and proliferating the cells obtained in (a) to obtain a pre-adipocyte clone; and
 (c) immortalizing a pre-adipose clone isolated under step (b).

Advantageously, the method typically further includes the steps of
(d) selecting for immortalized cells, and
(e) selecting for cells capable of differentiating into white adipose cells.

The present invention also relates to use of the adipose cells disclosed, and derived from the methods disclosed herein, in research studies directed to the role of white adipose tissue in the body. The immortalized cells are useful in identifying substances controlling the regulation of lipid uptake and release of normal white adipose cells and substances controlling the differentiation of pre-adipoytes into mature adipocytes. The present invention is further directed to methods of screening for compounds capable of controlling the expression of targets for obesity, cardio-vascular diseases, diabetes and compounds capable of regulating the secretion of any metabolites or hormones from human white adipocytes.

The present invention also relates to a means that allows an investigation of the effect of novel drugs or food ingredients on white adipose tissue.

In particular, the present invention provides novel pre-adipose cell lines derived from white adipose cells that have the capability to differentiate into mature white adipose cells, while exhibiting essentially the same cellular properties as do normal white adipose cells.

BRIEF DESCRIPTION OF THE DRAWINGS

In the figures,
FIG. 1 schematically shows how the pre-adipose cells were obtained.

DETAILED DESCRIPTION OF THE PREFERRED EMBODIMENTS

Figure 1:
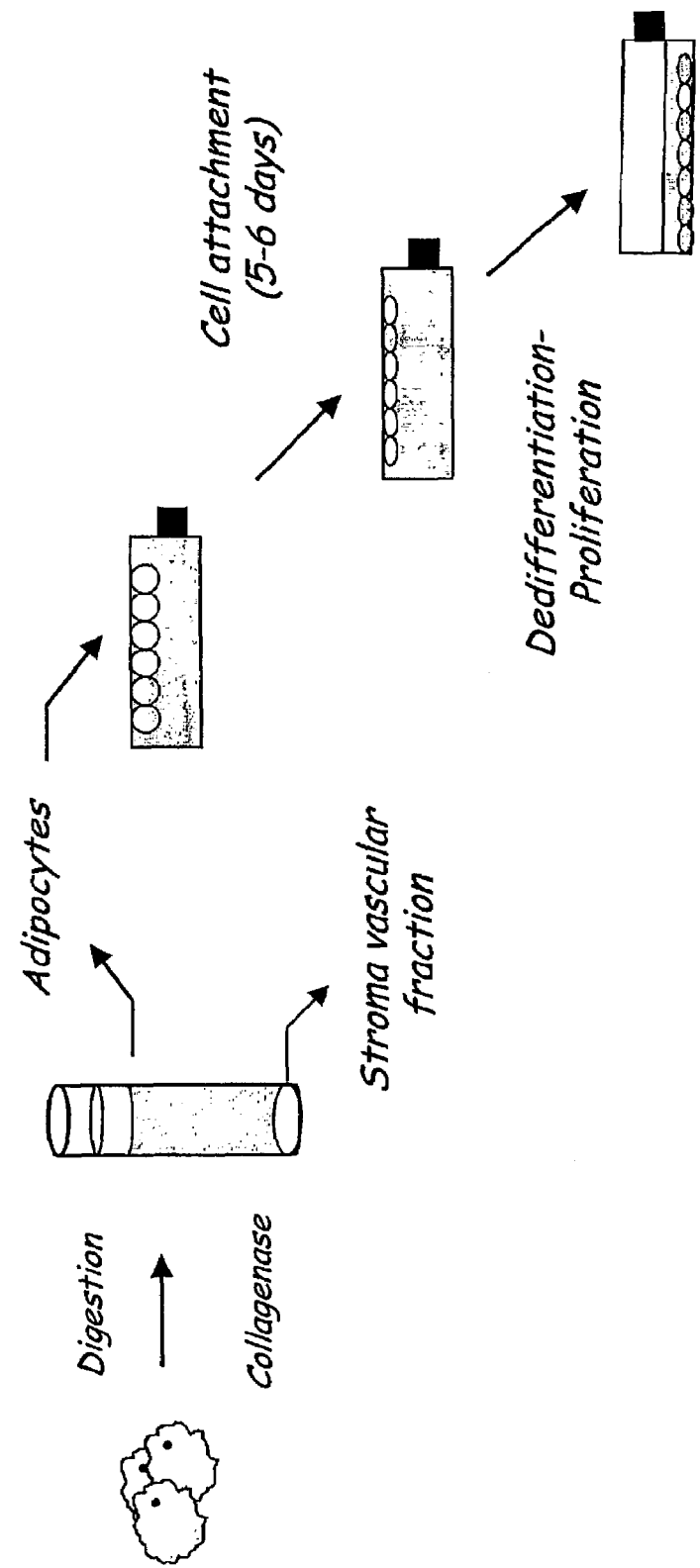
Figure 2:
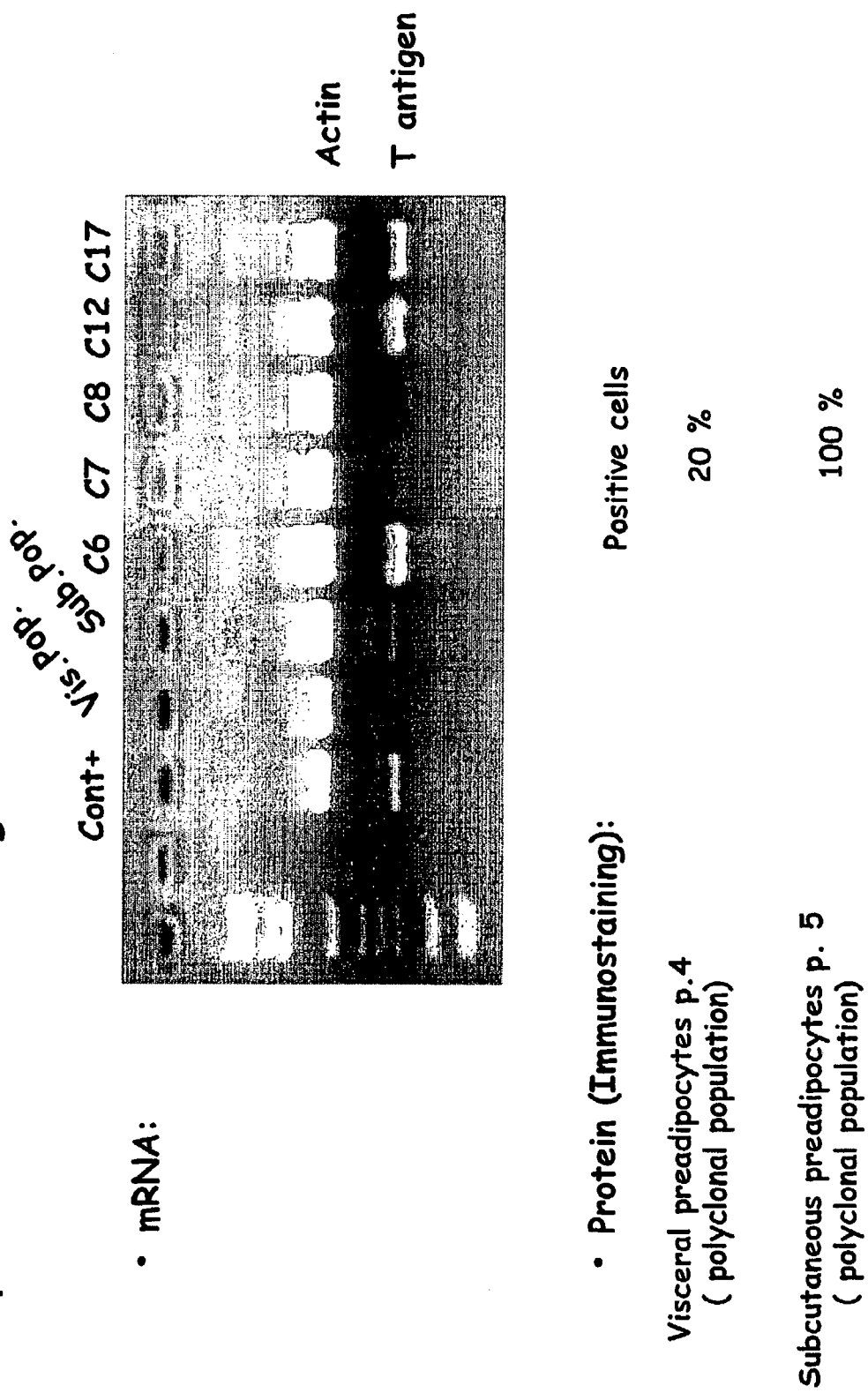
FIG. 2 shows the expression of the SV40 large T-antigen in the various immortalized clones analyzed by RT-PCR and immuno-fluorescence.
Figure 3:
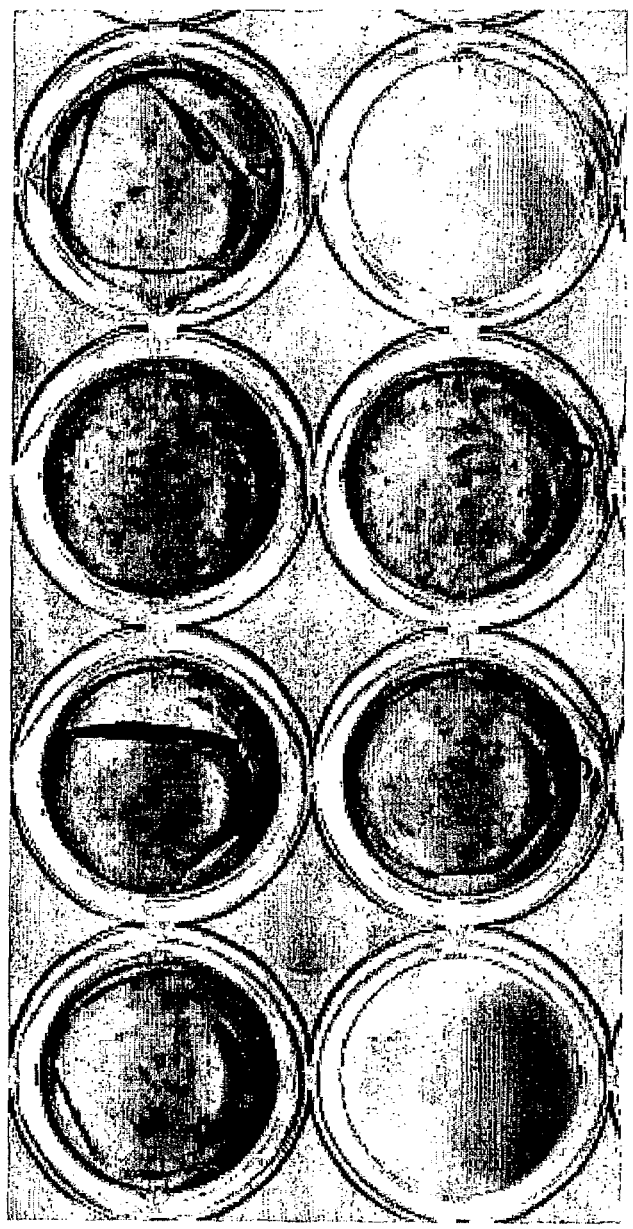
FIG. 3 shows the cell differentiation under different adipogenic conditions.
Figure 4:
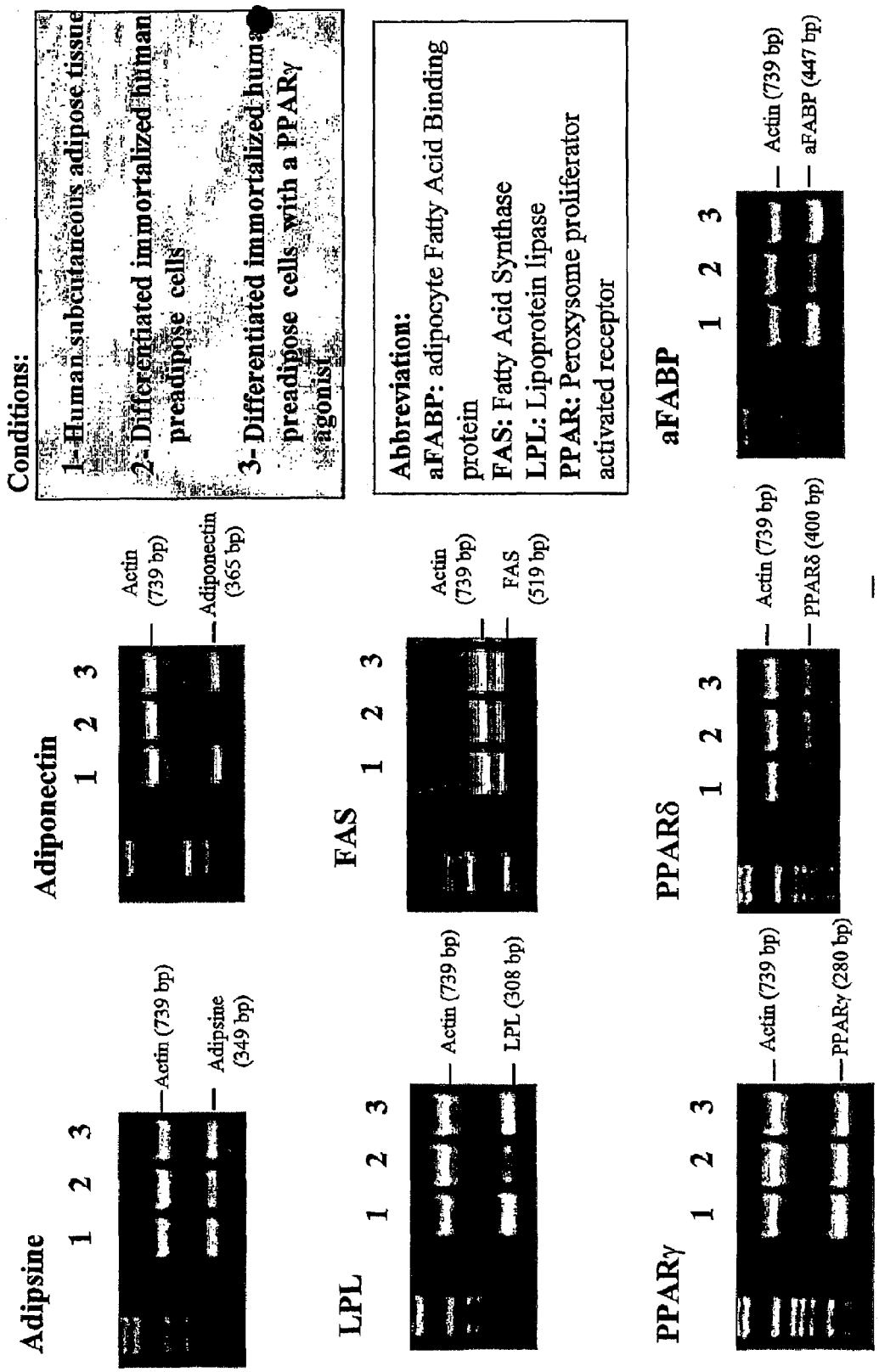
FIG. 4 shows the results of experiments investigating the expression pattern of different markers of adipocyte differentiation in the cell line as compared with human adipose tissue.

Cell lines have played an important role in the development of molecular and cellular biology, particularly in the elucidation of intracellular activities, the effects of extracellular molecules and cell-cell interactions. Cell lines are normally established stepwise by explantation of tissue containing a heterogeneous cell population, separation of the cells, isolation of a cell clone of interest and culturing the cell clone so that the total cell number increases over several generations and the population is uniform in its lineage. Yet these cells will survive only a limited number of passages in an in vitro culture before they start to senesce.

According to a preferred embodiment, the cell line is any of the cell lines deposited according to the Budapest Treaty with the Institute Pasteur at 28 Rue du Docteur Roux F-55724 Paris, France on Jul. 13, 2000, receiving the immortalized human pre-adipose cell line identified as ADScSV40-C6 and having Deposit No. CNCM I-2520, or on Apr. 27, 2001, receiving the immortalized human pre-adipose cell line identified as CHUB-S7 and having Deposit No. CNCM I-2663. Both CNCM I-2520 and CNCM I-2663 include the human papillomavirus E7 oncoprotein gene and the human telomerase reverse transcriptase gene.

The present invention now provides for novel immortalized cell lines capable of differentiate and to mature to white adipocytes. These immortalized adipocytes exhibit essentially the same morphological pattern as do normal white adipocytes obtained from living tissue, i.e., the polypeptide expression or cellular appearance.

The following abbreviations are used herein: aP2: Adipocyte fatty acid binding protein; BSA: bovine serum albumin; C/EBPα: CCAAT/enhancer binding protein alpha; Dex: Dexamethasone; FAS: Fatty Acid Synthase; FBS: fetal bovine serum; GPDH: Glycerol-3-phosphate dehydrogenase; hTERT: human telomerase reverse transcriptase; HPV-E7: human papillomavirus E7 oncoprotein; IBMX: isobuthyl methyl xanthine; LPL: Lipoprotein lipase; OA: oleic acid; PPARγ: peroxisome proliferator-activated receptor gamma; RPLp0: Ribosomal Preotein Large P0; SV40 T-Ag: SV40 T-antigen; and TRAP: telomerase repeat application protocol.

The term "normal human white adipose cell" shall mean a non-immortalized human white adipose cell that is not tumorigenic.

"Chub-S7" refers to the cells derived from deposit CNCM I-2663.

Having a metabolic pattern "essentially identical or the same" shall mean an immortalized mature white adipose cell that express at least four normal human white adipose cell markers selected from the group consisting of: lipoprotein lipase; fatty acid synthase; adipocyte fatty acid binding protein; leptin; adipsin; adiponectin; peroxisome proliferator-activated receptors γ; peroxisome proliferator-activated receptors β; CCAAT/enchancer binding protein alpha; and hormone sensitive lipase.

The present invention is directed to a culture of an immortalized human pre-adipose cell line and to methods of preparing the same. The culture of the present invention includes immortalized human pre-adipose cells capable of maturing into a immortalized mature white adipose cells. The mature adipose cells derived from the cell line exhibit metabolic patterns of normal human white adipose cells making them extremely useful for use in research and development programs. Typically, when the immortalized mature cells are cultured on serum-free medium they express at least four normal human white adipose cell markers selected from the group consisting of: lipoprotein lipase; fatty acid synthase; adipocyte fatty acid binding protein; leptin; adipsin; adiponectin; peroxisome proliferator-activated receptors γ; peroxisome proliferator-activated receptors β; CCAAT/enchancer binding protein alpha; and hormone sensitive lipase. Preferably, the immortalized cells express the following normal adipoctye markers lipoprotein lipase; leptin; adiponectin; and peroxisome proliferator-activated receptors γ and more preferably, they also express CCAAT/enhancer binding protein alpha, adipocyte fatty acid binding protein or adipsin.

The immortalized white adipose cell produced from the pre-adipose cell line has a karypotpe identical to a normal white adipose cell.

The pre-adipose cell lines of the present invention may be differentiated to mature white adipocytes with compounds known in the art, such as insuline, triiodothyronine, dexamethasone and activators of peroxisome proliferator-activated receptors (PPAR). The white adipocytes thus obtained will then essentially show the same metabolic markers as do normal white adipose cells, such as enzymes involved in triglyceride synthesis, e.g. lipoprotein lipase and fatty acid synthase, adipocyte fatty acid binding protein, leptin, adipsin, adiponectin, peroxisome proliferator-activated receptors γ and β (PPAR γ, β) and the hormone sensitive lipase. The white adipocytes may be kept in culture for at least 12 passages, preferably at least 20 passages, more preferably at least 30 passages and most preferably at least 50 passages.

According to a preferred embodiment the cell line is any of the cell lines deposited according to the Budapest Treaty with the Institute Pasteur at 28 Rue du Docteur Roux F-55724 Paris, France on Jul. 13, 2000, receiving the Deposit No. CNCM I-2520 or on Apr. 27, 2001, receiving the Deposit No. CNCM I-2663.

The present invention is also directed to a method for preparing an immortalized pre-adipose cell line capable of maturing into mature white adipose cells that exhibit essentially identical metabolic patterns as normal white adipose cells. The methods generally comprises the following steps:

(a) separating cells from a human adipose tissue;
(b) de-differentiating and proliferating the cells obtained in (a) to obtain a pre-adipocyte clone; and
(c) immortalizing a pre-adipose clone isolated under step (b).

Advantageously, the method typically further comprises the steps of (d) selecting for immortalized cells, and
(e) selecting for cells capable of differentiating into white adipose cells.

During step (a) white adipose cells are isolated in vitro from an appropriate adipose tissue from a human donor. The primary tissue obtained from the donor is first treated such that the adipocytes are separated from other cells present, such as, e.g., by treatment of the tissue sample with a solution containing collagenase and separating adipocytes from the other cells by successive filtrations followed by a centrifugation.

In the subsequent step (b) the adipose cells obtained in step (a) are de-differentiated, which may be effected by using e.g. the so called "ceiling culture method" previously described for rodent adipocytes (Sugihara H., Yonemitsu N., Miyabara S., Yun K. 1986, Primary culture of unilocular fat cells: characteristics of growth in vitro and changes in differentiation properties, *Differentiation*, 31: 42-49). According to this method the adipocytes are transferred into a culture flask, that is filled to the top with culture medium and positioned upside down. After six days under these conditions, adipocytes de-differentiated spontaneously into fibroblast-like cells deprived of lipid droplets. The resulting de-differentiated adipocytes are then proliferated under the same culture condition as above to obtain actively growing pre-adipocytes.

In the next step (c) the pre-adipocytes thus obtained are immortalized. This may be achieved by infecting cells with a recombinant vector, such as with a recombinant plasmid, a recombinant virus or a retrovirus, e.g. a recombinant retroviral vector carrying the large T antigen gene of SV40 virus (Simian Virus) or the E6 or E7 genes of HPV virus (Human Papilloma Virus). According to an alternative method the recombinant vector harbors the telomerase reverse transcriptase (TERT) genes, which are preferably derived from the same species as the cells being immortalized. The gist of the latter method resides in essentially preventing the shortening of the chromosome's telomeres. Telomere shortening has been linked with senesce of cells. Telomere maintenance and cellular immortalization has been reported in epithelial cells by Kiyono et al, *Nature* 396 (1998), 84-88, which document is incorporated herein by way of reference.

A successive infection with SV40 virus (Simian Virus) or the E6 or E7 genes of HPV virus and the TERT gene represents also an alternative method for human pre-adipocyte immortalization.

In the subsequent step (d) a selection is made for cells positively immortalized, which may e.g. simply be performed by culturing cells obtained in step (c) for several passages or by testing the cells for genes of the vector used for the immortalization, such as for genes from the SV40 virus or genes from the HPV virus. This may be achieved by detecting the expression of the respective genes by means of antibodies or may involve an analysis via PCR-techniques. The expression of the telomerase reverse transcriptase genes is detected by measuring the telomerase activity determined by applying the Telomerase Repeat Amplification Protocol (TRAP).

In the subsequent step (e) the cells shown to be positively immortalized by the introduction of the vector are tested for their ability to differentiate into mature white adipose cells. To this end, the cell lines obtained under step (d) are treated with common differentiating agents, such as detectable by intracellular lipids staining. Lipids staining is commonly performed with the Oil-red-O method which specifically stains lipids.

The cell lines of the present invention may be used for different purposes, such as serving as a means to investigate the role of controlling the regulation of lipid uptake and release by white adipocytes, or the identification of substance controlling the differentiation of pre-adipocytes into mature adipocytes, or for screening for compounds capable to control the expression of targets for obesity, diabetes and cardio-vascular diseases. Particularly, these cell lines may be helpful for the screening of factors able to regulate the release by adipocytes of compounds involved in the control energy metabolism such as leptin.

EXAMPLES

The following examples will illustrate the invention without limiting it to the specific embodiments mentioned.

Example 1

Adipocyte Extraction from Human Subcutaneous Adipose Tissue

After surgery the biopsy of subcutaneous adipose tissue from an obese patient was maintained at room temperature with a mixture of Dulbecco's modified Eagle's medium (DMEM) and Ham's F12 media (v/v) (Gibco BRL) supplemented with 10% fetal calf serum (FCS) (Gibco BRL), 100 µg/ml streptomycine/penicilline and 2 mM glutamine. This medium was termed basic medium. The adipose tissue was minced into small pieces and digested 20 min at 37° C. into 3 ml of digestion medium per gram of tissue. The digestion medium contained 2 mg/ml collagenase (Roche Biomedical) and 20 mg/ml bovine serum albumin (Sigma) dissolved into DMEM medium.

Digestion was stopped by the addition of an equivalent volume of FCS in order to get a 20% FCS concentration. The digested fluid was filtered twice with filters of different porosity (250, 100 µm) and centrifuged 10 min at 1000 rpm. Adipocyte fraction was obtained as a thin and white floating layer which was removed and put into 30 ml phosphate buffer at 37° C. The suspension was centrifuged (10 min at 1000 rpm) in order to obtain an adipocyte fraction deprived of other contaminating cells.

Example 2

Primary Adipocyte Dedifferentiation and Proliferation

About $10^6$ adipocytes were incubated in a 25 cm$^2$ flask completely filled with DMEM mixed with Ham's F12 medium (v/v) supplemented with 20% FCS, 10 mg/ml streptomy-cine/penicillin and 2 mM glutamine. The flask was turned upside down in order to allow adipocytes to adhere to the top inner surface. After 8 days of culture in the appropriate environment (37° C., 90% humidity) cells had attached and started to de-differentiate spontaneously into pre-adipocytes and to proliferate. The flask was then turned in the proper orientation and the medium was removed. 5 ml of the above described basic medium was added in the flask. After 2 days under these conditions cells were infected.

Example 3

Cell Immortalization

1. Production of Retrovirus

A recombinant retroviral vector carrying the large T antigen gene of SV40 virus (Simian Virus) or the E6/E7 genes of HPV virus (Human Papilloma Virus) or the human telomerase reverse transcriptase (hTERT)) were constructed by insertion, with standard recombinant DNA techniques, into the BamHI site of the pLHXSD retroviral vector (Stockschlaeder et al., *Hum Gene Ther.*, 2 (1991), 33-39) containing the histidinol gene as selection marker.

Infectious recombinant virus particles were generated through transfection of the recombinant retroviral vector into the amphotropic packaging cell line Phoenix (Clontech), followed by co-culturing with the ecotropic packaging cell line, Psi2 (ATCC) to allow "ping-pong" infection to produce a high-titer virus (Lynch C, Miller D. 1991. "Production of high helper virus-free retroviral vectors by coc-ultivation of packaging cells with different host recipes." *J. Virol.*, 65: 3887-3890).

2. Infection of Primary Adipose Cells

Infectious recombinant virus particles as prepared above were used to infect primary human de-differentiated adipose cells obtained according to example 2. The cells were incubated for 3 hours at 37° C. (90% humidity) with the recombinant virus in the presence of 20 µg/ml DEAE dextran. After the infection, the culture medium was changed with the basic medium.

Ten days after infection the first clones were picked up by aspiration and expanded separately. The expression of the SV40 T antigen or E7 genes in the different clones was determined by RT-PCR using SV40 T antigen: 5'GGATTCAGTGGTGTATGACT; (SEQ ID No. 1)

5'AGGCACACTGTACTCATTCA; (SEQ ID No. 2)

E7: 5'GGAGATACACCTACATTGCA; (SEQ ID No. 3)

5'GATGGGGCACACAATTCCTA (SEQ ID No. 4)

(all purchased from Microsynth);

and immuno-staining utilizing mouse monoclonal antibodies directed against the human SV40 T antigen (Oncogene). The telomerase activity was determined by applying the Telomerase Repeat Amplification Protocol (TRAP) according to Kim et al., *Science* 266 (1994), 2011-2015.

Example 4

Differentiation of Infected Cells

7SV40 T antigen, E7, TERT or E7 and TERT positive cells as obtained in example 3 were incubated in the basic medium, as defined in example 1, to confluence at which stage an adipogenic cocktail was added to the medium which cocktail contained the basic medium and supplemented with 850 nM insulin; 10 pg/ml transferrin; 1 nM triiodothyronine; 500 µM fetuin, 33 µM panthotenic acid, 1 mM Hepes, 15 mM NaHCO$_3$ and 1 µM dexamethasone and 1 µM BRL49653, a PPARγ agonist. Incubation of the cells was continued. At day 10 after confluence cells started to exhibit an adipocytic phenotype with intracellular lipid droplets observed with a specific staining. This Oil-red-O staining was performed on fixed cells with 10% Formaldehyde incubated 2 hours with the dye dissolved at in isopropanol. Cells were then washed with water and observed under microscope. Differentiated adipocytes appeared as cells filled with red cytoplasmic spots corresponding to the accumulation of lipid droplets.

Example 5

Expression of Adipocytes in Differentiated Immortalized Human Pre-adipose Cells

Confluent immortalized human pre-adipose cells of the cell line CNCM I-2550 (as obtained in the preceding examples) were cultured in a serum-free chemically defined medium described in Example 4.

At day 17 after confluence, cells were washed with Hank's balanced salt solution and RNA was extracted using the RNeasy Total RNA Purification System (Qiagen AG, Switzerland). Reverse transcription was performed with an input of 2 µg of total RNA using the 1$^{st}$ strand cDNA synthesis kit for RT-PCR (AMV; Roche Biomedical, Switzerland) with oligo d(T)$_{15}$ as primer. Primers used for the amplification of cDNA's of interest are listed below in Table 1 and were synthesized by Mycrosynth (Windisch, Switzerland).

The PCR reaction was heated for 2 cycles to 98° C. for 1 min, 60° C. for 2 min and 72° C. for 2 min and then cycled 28 times through a 1 min denaturation step at 94° C., a 1 min annealing step at 60° C. and a 2 min extension step at 72° C. in a DNA thermal cycler apparatus (Bioconcept, Allschwil, Switzerland).

Actin primers were included in the reaction as an internal control. PCR products (10 µl) were separated on a 2% agarose gel and visualized by ethidium bromide staining.

The results clearly indicate that the cell line investigated expresses the respective adipocyte's markers in a manner essentially identical to normal human adipose tissue as such.

Essentially identical to normal white human adipose tissue shall mean a culture of a human pre-adipose cell line capable of maturing into a white adipose cell, wherein the adipose cell differentiated from the pre-adipose cell line exhibits identical metabolic functions that normal human white adipose express adipocyte markers. These data demonstrate, for the first time, that co-expression of hTERT and HPV-E7 in human pre-adipocytes allows cells, not only to display an indefinite life span but also to retain their capacity to differentiate.

Example 6

Preparation of Cell Line CNCM I-2663
(CHUB-S7)

Proliferation of primary cells is limited a few population doublings (PDs) before entering into a phase of growth arrest called replicative senescence. Overexpression of viral oncogenes such as the SV40 T-antigen (SV40 T-Ag) has been widely used to overcome senescence and to promote

TABLE 1

| | |
|---|---|
| Actin | Forward 5'-GTTGCTATCCAGGCTGTG-3' (SEQ ID No. 5) |
| | reverse 5'-CATAGTCCGCCTAGAAGC-3' (SEQ ID No. 6) |
| Adipsine | forward 5'-TACAGCTGTCGGAGAAGG-3' (SEQ ID No. 7) |
| | reverse 5'-TTCTTGCGGTTGCCGCAAAC-3' (SEQ ID No. 8) |
| Adiponectin | forward 5'-GGGAGCTGTTCTACTGCTAT-3' (SEQ ID No. 9) |
| | reverse 5'-CTCCAATCCCACACTGAATG-3' (SEQ ID No. 10) |
| Fatty Acid Binding protein (aFABP) | forward 5'-GGTACCTGGAAACTTGTCTC-3' (SEQ ID No. 11) |
| | reverse 5'-AACTTCAGTCCAGGTCAACG-3' (SEQ ID No. 12) |
| Lipoprotein Lipase (LPL) | forward 5'-TTTCTCTGTATGGCACCGTG-3' (SEQ ID No. 13) |
| | reverse 5'-TTCACAAATACCGCAGGTGC-3' (SEQ ID No. 14) |
| Fatty Acid Synthase (FAS) | forward 5'-GGTCTTGAGAGATGGCTTGC-3' (SEQ ID No. 15) |
| | reverse 5'-CAGGTTGACAGCAGCCAAGT-3' (SEQ ID No. 16) |
| Peroxysome proliferator acivated recceptor γ (PPAR γ.) | forward 5'-TCAACGACCAGGTTACCCTT-3' (SEQ ID No. 17) |
| | reverse 5'-CTTGATCCGCTGCATCATCT-3' (SEQ ID No. 18) |
| Peroxysome proliferator acivated recceptor γ (PPAR γ) | forward 5'-GTGCAGGAGATCACAGAGAT-3' (SEQ ID No. 19) |
| | reverse 5'-TTGCCAAGTCGCTGTCATCT-3' (SEQ ID No. 20) |

Overexpression of SV40 T-antigen (SV40 T-Ag) has been widely used to overcome replicative senescence of human primary cells and to promote cell immortalization. However, in the case of certain cell types, such as pre-adipocytes, the differentiation process of immortalized cells is blocked by SV40 T-Ag expression. In this study, human telomerase reverse transcriptase (hTERT) and papillomavirus E7 oncoprotein (HPV-E7) genes were co-expressed in human pre-adipocytes to test whether this combination could maintain cell differentiation capacity after immortalization. We demonstrated that the HPV-E7/hTERT expressing pre-adipocytes displayed an indefinite life span. Interestingly, immortalized cells were diploid and presented no chromosomic alterations. These immortalized cells were able to accumulate and to hydrolyse intracellular triglycerides and to human cell immortalization (1). However, ectopic expression of viral oncogenes allows primary cells to overcome replicative senescence, only for a few PDs before entering into a second non-replicative phase called "crisis" (2). In most cell types, rare cellular clones are able to escape from crisis and to proliferate indefinitely (3). This limitation in the immortalization process of human cells can be overcome by the reconstitution of the telomerase activity. Indeed, it has been recently shown that overexpression of the human telomerase reverse transcriptase (h-TERT) allows SV40 T-Ag transformed cells, derived from different tissues, to bypass the crisis step and to promote indefinite life span (4-8). Nevertheless, the differentiation process of certain cell types, such as pre-adipocytes, is clearly blocked by SV40 T-Ag expression (9, 10).

Differentiation of pre-adipocytes into adipocytes (i.e. adipogenesis) is a well-described system regulated by various factors. Upon induction of differentiation, a cascade of gene transcription events occurs, leading to the expression of adipocyte-specific genes (11). This adipocyte differentiation cascade is controlled by two key transcritional factors the peroxisome proliferator-activated receptor gamma (PPARγ) and the CCAAT/enhancer binding protein alpha (C/EBPα). The cAMP-response element-binding protein-binding protein (CEBP) and its highly related p300 protein have been recently shown to be necessary for the induction of both PPARγ and C/EBPα (12, 13). Interestingly, SV40 T-Ag interacts with both CBP and p300, inhibiting their co-activation function (14, 15). These observations could explain why a previous attempt to immortalize human pre-adipocytes derived from white adipose tissue with SV40 T-Ag has failed to deliver permanent cell lines showing a preserved capacity for differentiation (16).

The E7 oncoprotein from the human papillomavirus type 16 (HPV-E7) has also been reported as a factor promoting human cell immortalization (17). However, immortalization by HPV-E7 alone is a rare event. Coexpression of HPV-E7 and hTERT was shown to increase the frequency of immortalization of human keratinocytes (Kiyono, 1998 #14). Interestingly, unlike SV40 T-Ag, HPV-E7 does not bind to CBP/p300 (18), shown that overexpression of HPV-E7 in human pre-adipocytes could preserve their adipogenic capacity.

In this context, we tested whether ectopic expression of HPV-E7 combined with the reconstitution of telomerase activity would allow establishment of a human white preadipose cell line with an indefine life span and a preserved adipogenic capacity. For this purpose, human pre-adipocytes from subcutaneous white adipose tissue were successively infected with recombinant viruses carrying hTERT and HPV-E7 genes. We showed that these transformed cells were able to proliferate indefinitely and to differentiate into lipid filled cells expressing adipocyte markers.

1. Results

A. Immortalization of Human Pre-adipocytes

Human primary pre-adipocytes were infected with a recombinant retrovirus carrying the hTERT gene. Several clones were obtained after histidinol selection. These cells were able to divide until about passage 12 before entering to senescence and growth arrest (not shown). The ability of these clones to differentiate into lipid filled adipocytes was tested using the Oil red-O staining, as described in Material and Methods. The clone presenting the best capacity to accumulate lipid was infected at passage 8 with retroviral particles containing the HPV-E7 gene. After infection, cells started to proliferate more rapidly than cells infected with hTERT alone. These cells were able to grow with a doubling time of 45.6±0.8 h, without any modifications in cell proliferation, until at least 176 PDs (passage 46). This cell line considered as immortal was named Chub-S7. Chub-S7 cells expressed HPV-E7 gene as detected by RT-PCR (data not shown) and presented a telomerase activity (FIG. 5) which was maintained until, at least, 145 PDs (passage 38; not shown)

B. Karyotype Analysis

Figure 6:
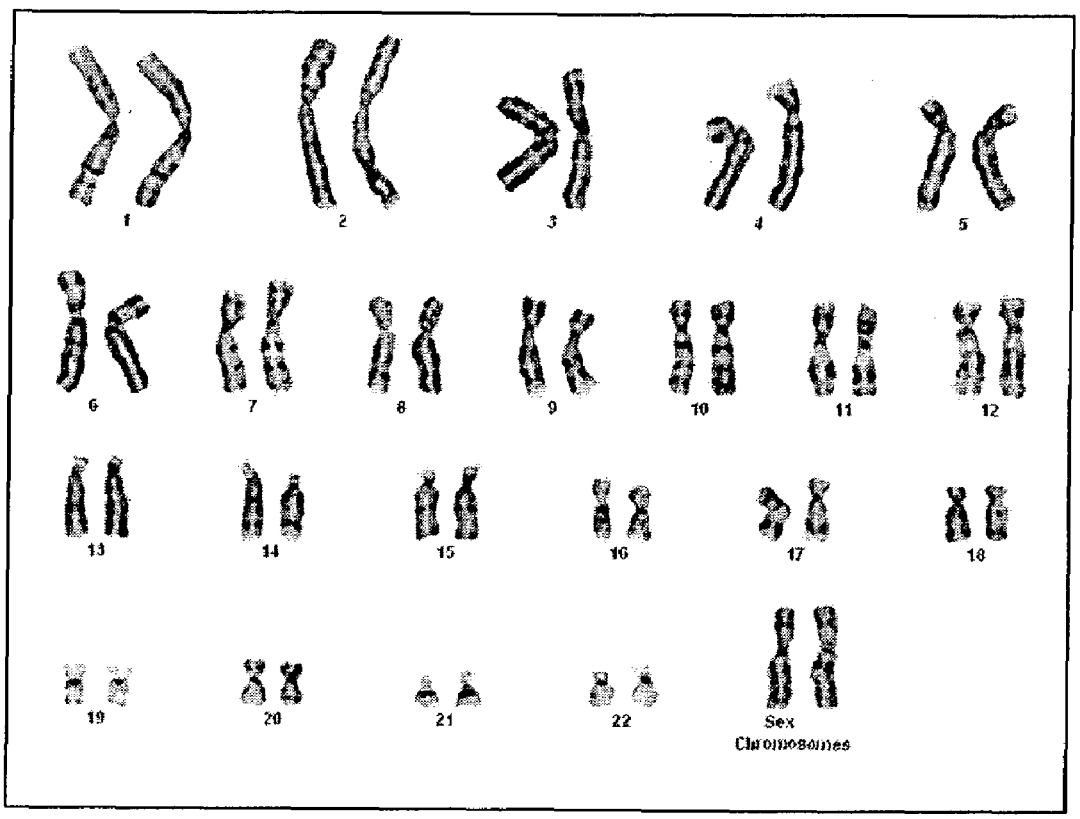
FIG. 6 shows the results of a karyotype analysis of Chub-S7 cells.

To determine whether this cell line presented chromosomic alterations that may affect cell phenotype, the chromosome pattern of Chub-S7 cells was analyzed at 81 and 157 PDs (passages 21 and 41, respectively). The karyotype analysis showed that Chub-S7 cells were diploid with 46, XX chromosomes (FIG. 6). Chromosomes did not present any apparent abnormalities at low and high passages.

C. Differentiation Capacity of Chub-S7 Cells

Adipocyte differentiation of Chub-S7 cells was tested under serum-free culture conditions. To promote pre-adipocyte differentiation, confluent cells were incubated with a basal medium (see Material and Methods) supplemented with 500 μM IBMX and 1 μM Dex for the first 3 days, and 1 μM of a PPARγ agonist (BRL49653) and 1 μM Dex from day 3 to 17. This condition was compared to the basal medium alone or supplemented with Dex plus IBMX from day 0 to 3 and Dex alone from day 3 to 17. To determine whether Chub-S7 cells were able to differentiate, the expression of adipocyte markers was assessed, by real-time RT-PCR, at different time points during cellular maturation. These markers included i) transcriptional factors involved in adipogenesis such as peroxisome proliferator-activated receptor γ (PPARγ) and CAAT/enhancer binding protein α (C/EBPα), ii) genes involved in lipid metabolism such as lipoprotein lipase (LPL) and adipocyte fatty acid binding protein (aP2), and finally iii) adipocyte secreted factors such as adipsin and leptin.

Figure 7:
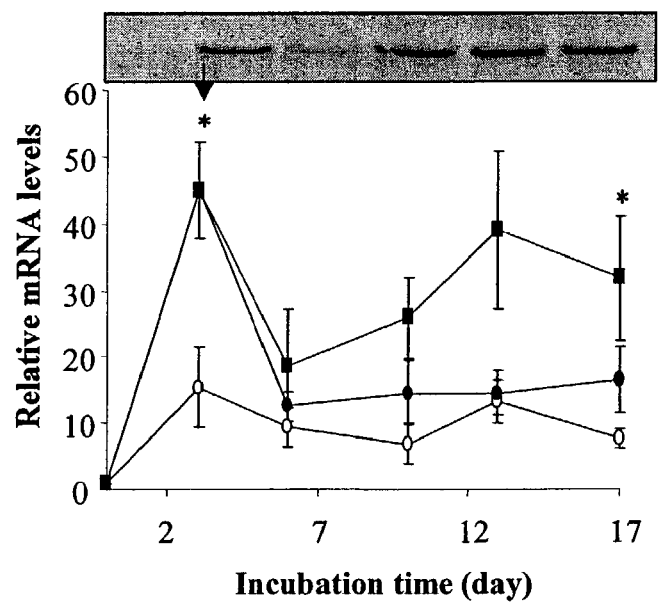
FIG. 7 shows the profile of peroxisome proliferator-activated receptor gamma and CCAAT/enhancer binding protein alpha gene expression during Chub-S7 cell differentiation.
Figure 7:
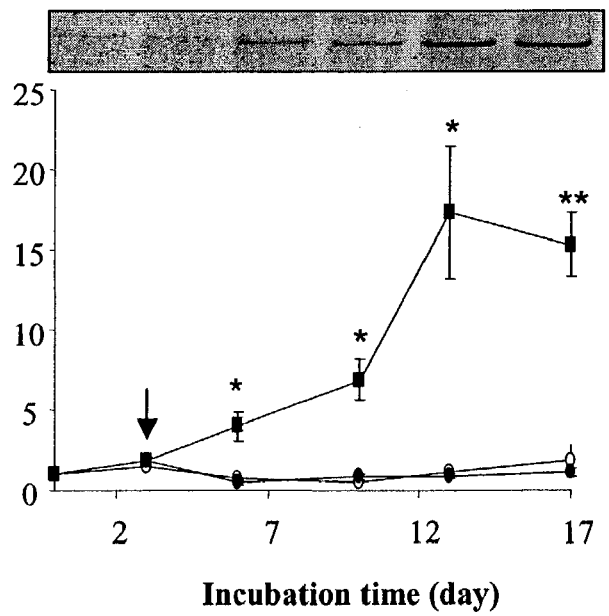

Under basal conditions, PPARγ was increased by about 10-fold at day 3 as compared to day 0 and remained constant until day 17. After incubation with Dex plus IBMX, PPARγ mRNA were increased by about 35-fold at day 3 as compared to day 0 (FIG. 7). After IBMX removal, PPARγ mRNA fell to the basal level, but BRL49653 was able to reinitiate PPARγ expression at day 10 and 17. In presence of BRL49653, C/EBPα mRNA was slightly increased as early as day 6 after confluency and reached a plateau at day 13 (FIG. 7). Basal medium supplemented or not with Dex alone did not affect C/EBPα expression along the time course.

Figure 8:
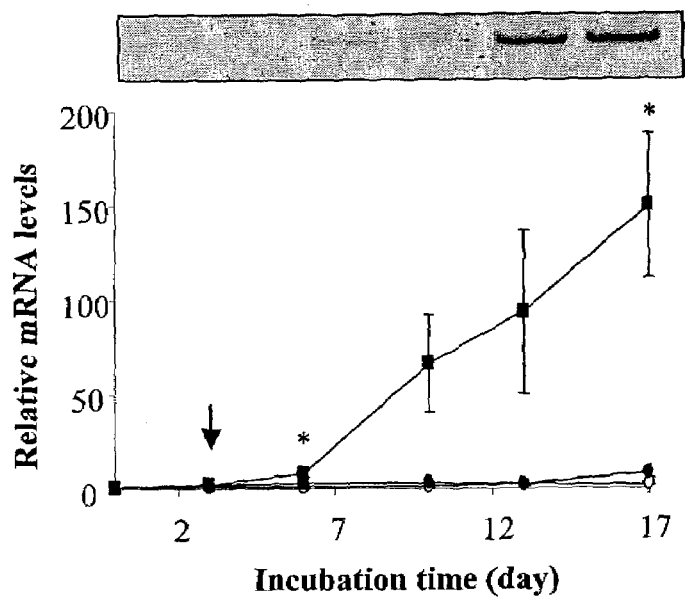
FIG. 8 shows the profile of lipoprotein lipase and adipocyte fatty acid binding protein gene expression during Chub-S7 cell differentiation.
Figure 8:
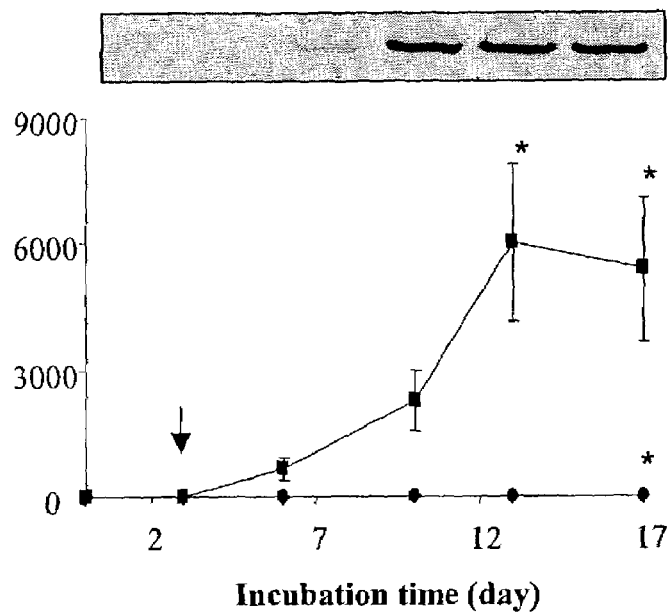

Cells cultured in presence of the PPARγ agonist showed increased levels of aP2 and LPL mRNA as early as day 3 and day 6 after confluency, respectively (FIG. 8). This expression continued to increase up to day 17 for both genes. Dex alone was able to enhance significantly aP2 and LPL mRNA expression at day 17 as compared to day 0, but to a lesser extent to that observed in presence of the PPARγ agonist (8 vs. 8372 fold-increase for aP2 and 16 vs 308 fold-increase for LPL).

Figure 9:
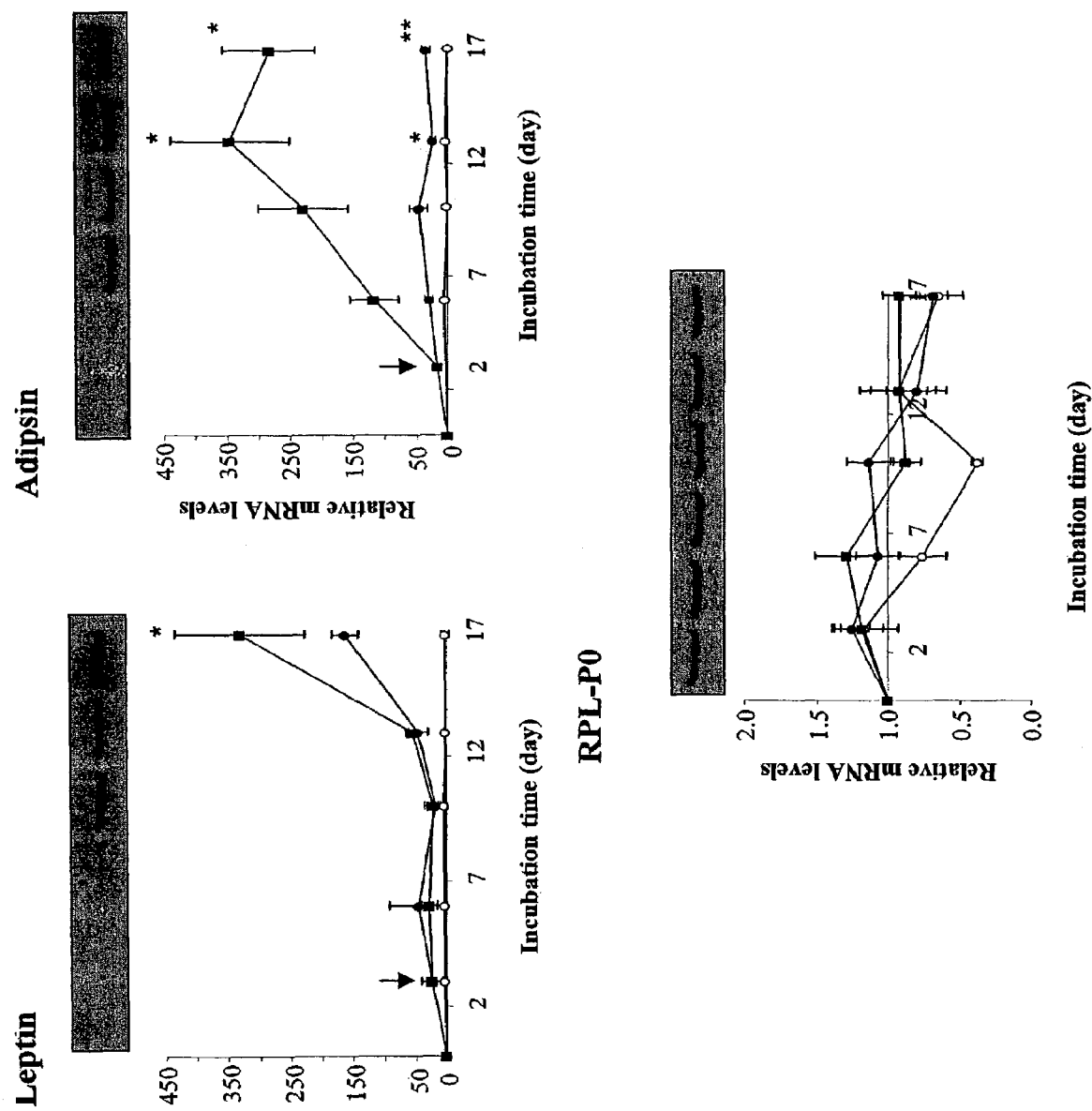
FIG. 9 shows the profile of adipsin, leptin and RPL-P0 gene expression during Chub-S7 cell differentiation.

Adipsin mRNA levels reached a plateau as early as at day 10 whereas the highest leptin mRNA expression was observed only at day 17 (FIG. 9). Before day 17, the increase in leptin mRNA was similar in presence or in absence of the PPARγ agonist but was 2 fold higher at day 17, in presence of BRL49653 when compared to Dex alone. The expression of the ribosomal protein large P0 used in this study for normalization, showed no changes in mRNA levels during Chub-S7 cell differentiation (FIG. 9).

These results show that under conventional serum-free culture conditions, differentiated Chub-S7 cells were able to acquire the main adipocyte markers.

D. Functional Characteristics of Differentiated Chub-S7 Cells

To study the ability of differentiated Chub-S7 cells to accumulate intracellular lipids, cells cultured for 17 days in the absence or in the presence of BRL49653 were fixed and stained with Oil-red O. Almost all the differentiated cells were able to accumulate at least one single lipid droplet and few of them presented large multilocular droplets (FIG. 10B). When OA (100 μM complexed with BSA) was added from day 10 to 17 to the differentiation medium containing BRL49653, Chub-S7 cells showed a dramatic increase in their triglyceride content with large multilocular lipid droplets (FIGS. 10A-10B). The presence of OA did not affect the expression of LPL, C/EBPα, aP2, leptin and adipsin induced by BRL49653 (data not shown).

Lipolytic capacity of differentiated cells was assessed by measuring glycerol release, after stimulation or not for 1 h with 1 µM isoproterenol (Iso), a non-specific β-adrenergic agonist. Cells were differentiated in the presence of BRL49653 alone. Iso significantly increased by 40.5% lipolysis in cells cultured in the presence of the PPARγ agonist (FIG. 11A).

The glycerol-3-phosphate dehydrogenase (GPDH) is a key enzyme involved the glycerol phosphate shuttle pathway. Its activity was measured in Chub-S7 cells during differentiation. FIG. 10B shows that GPDH specific activity was slightly increased, at day 10, in presence of BRL49653 and reached a maximum level at day 17. Under basal conditions or with Dex alone, GPDH specific activity was not increased along the time course. (FIG. 11B).

2. Discussion

SV40 T-Ag, a well known immortalizing factor, has been shown to alter cell differentiation and especially to block the maturation of pre-adipocytes into adipocytes (9, 10). This inhibitory effect of SV40 T-Ag could explain the limited differentiation capacity of the SV40 T-Ag-transformed human white pre-adipocytes previously described (16). We demonstrate, for the first time, that co-expression of hTERT and HPV-E7 in human pre-adipocytes allows cells, not only display an indefinite life span but also to retain normal metabolic expression of primary cells.

We teach herein that pre-adipocytes derived from human white adipose tissue preserved their adipogenic capacity after immortalization by hTERT and HPV-E7 coexpression. This approach allowed, for the first time, the establishment of a human white preadipose cell line, which represents a useful model for studying pharmacological and nutritional regulations of adipocyte differentiation and metabolism.

Figure 5:
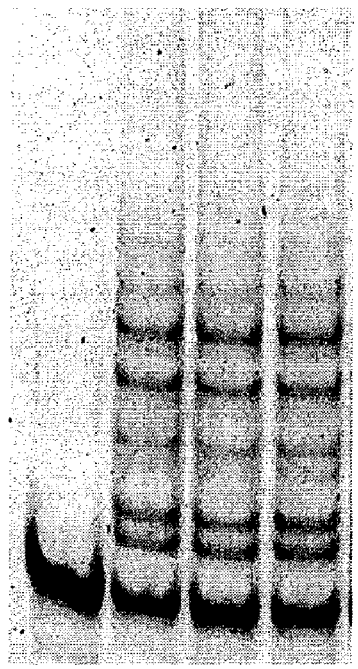
FIG. 5 shows the telomerase activity in the cells of CNCM I-2663 (also known as "Chub-S7").

Now turning to the figures for further illustration, in FIG. 5 the telomerase activity in Chub-S7 cells is shown. Telomerase activity was measured in confluent Chub-S7 cells at 73, 76 and 80 population doublings (PDs) using the TRAP assay. In the the first lane, the reaction was performed in the absence of cell lysates. Telomeric repeat amplifications were observed on the other lanes.

FIG. 6 shows a karyotype analysis of Chub-S7 cells. The cytogenetic analysis was performed on Chub-S7 cells at 96 PDs as indicated in Material and Methods below.

FIG. 7 shows the profile of PPARg and C/EBPa gene expression during Chub-S7 cell differentiation. Chub-S7 cells were cultured from day 0 to 17 in the presence of the basal medium as defined in Material and Methods (m), or in the basal medium with 1 µM Dex plus 500 µM IBMX from day 0 to 3 and dexamethasone from day 3 to 17 (●) or supplemented with 1 µM BRL49653 (■). The arrow indicates the day from which BRL49653 was added to the medium. Relative gene expression was quantified by real-time RT-PCR. Data are the means±SEM of values obtained at least in four separate experiments. Values significantly different from the basal conditions at defined days during the time-course are indicated by * ($P<0.05$) or ** ($P<0.01$). Top panels show representative RT-PCRs performed at a number of cycle defined according to the linear amplification of the genes (see Material and Methods).

FIG. 8 shows the profile of LPL and aP2 gene expression during Chub-S7 cell differentiation. See legend to FIG. 7 above.

FIG. 9 shows the profile of adipsin, leptin and RPL-P0 gene expression during Chub-S7 cell differentiation. See legend to FIG. 7 above.

Figure 10:
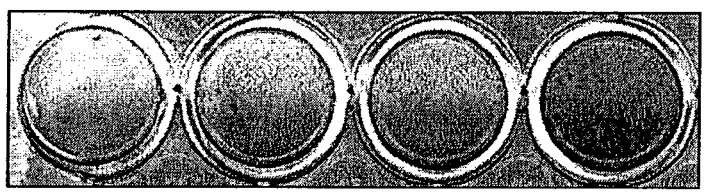
FIG. 10 shows the triglyceride accumulation in differentiated Chub-S7 cells.
Figure 10:
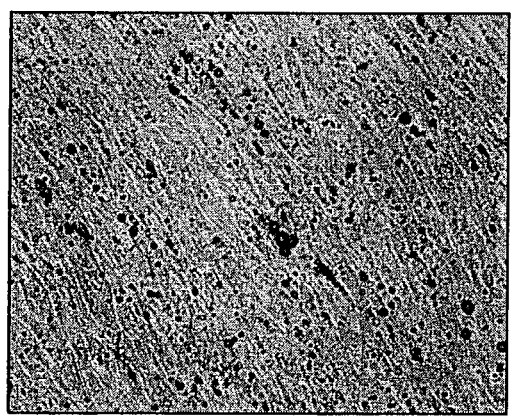
Figure 10:
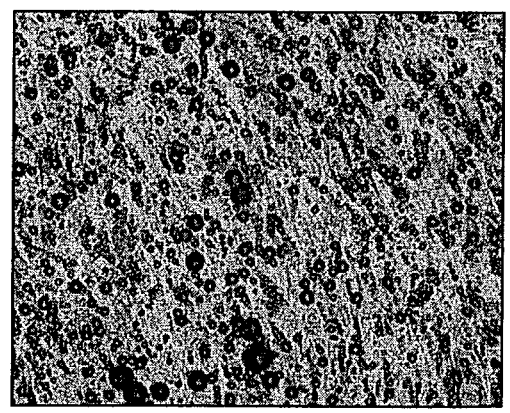

FIG. 10 shows the triglyceride accumulation in differentiated Chub-S7 cells. Chub-S7 cells were grown in the presence of the basal medium with 1 µM dexamethasone plus 500 µM IBMX from day 0 to 3 and Dex from day 3 to 17 or supplemented with 1 µM BRL49653 alone or in the presence of 100 µM OA from day 10 to 17. At day 17, cells were fixed and triglycerides were visualized using the oil-red O staining. A: Staining of culture wells containing Chub-S7 cells differentiated under the conditions described above. B: Morphology of Chub-S7 cells differentiated with dexamethasone and BRL49653 or in the same medium supplemented with oleate (Magnitude 400×). Data are representative of at least 3 independent experiments.

Figure 11:
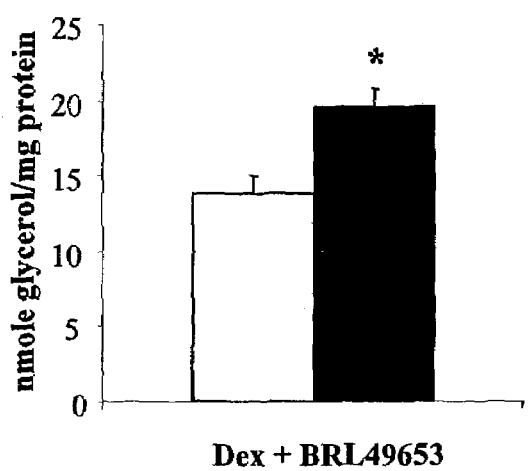
FIG. 11 shows the functionality of differentiated Chub-S7 cells.
Figure 11:
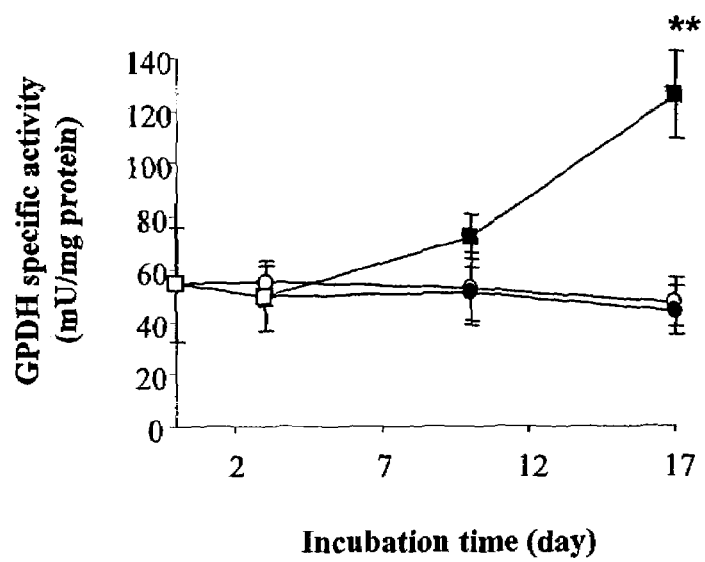

FIG. 11 shows the functionality of differentiated Chub-S7 cells. A. Chub-S7 cells were differentiated in the presence of 1 µM Dex plus 500 µM IBMX from day 0 to 3 and dexamethasone plus 1 µM BRL49653 from day 3 to 17. Glycerol released in the medium was measured in the presence or in the absence of 1 µM isoproterenol. Data are the means of values obtained at least in four separate experiments. Values significantly different from the basal condition of cells differentiated with BRL49653 only are indicated by * ($P<0.05$). B. Chub-S7 cells were cultured from day 0 to 17 in the presence of the basal medium (m), or in the basal medium with 1 µM Dex plus 500 µM IBMX from day 0 to 3 and Dex from day3 to 17 (●) or supplemented with 1 µM BRL49653 (■). Data are the means±SEM of values obtained at least in four separate experiments. Values significantly different from the basal condition at defined days during the time-course are indicated by ** ($P<0.01$).

3. Material and Methods

A. Materials

Cell culture media, fetal bovine serum (FBS) and Hepes buffer were purchased from Gibco BRL (Basel; Switzerland). Fetuin, transferrin, histidinol, insulin, triiodothyronin, dexamethasone, isobuthyl methyl xanthine (IBMX), biotin, d-panthotenic, oleic acid were purchased from Sigma (Buchs; Switzerland). NaHCO$_3$ was obtained from Merck (Darmstadt; Germany).

B. Recombinant Virus Preparation

Infectious hTERT recombinant viral particles were generated as previously described (8). The packaging cell line PA317 transfected with a retroviral construct consisted of the pLXSN vector containing the HPV-E7 gene (19) was kindly provided by Dr C. C. Harris (NCI, NIH, Bethesda). Viral particles were obtained through the ping-pong procedure as previously described (20).

C. Preparation and Infection of Human Pre-adipocytes

Adipocyte precursors from subcutaneous abdominal adipose tissue of a 33-year-old obese female, with a body mass index of 54, were prepared as previously described (21) and cultivated in a mix of DMEM/F 12 media (v/v) supplemented with 2 mM glutamine, 100 U/ml penicillin/streptamycin and 10% FBS. At 70-80% confluence, primary pre-adipocytes were incubated for 4 h at 37° C. and 5% CO$_2$ with recombinant retrovirus containing the hTERT gene in presence of 20 µg/ml DEAE dextran. After infection, the culture medium was changed to a mixture of DMEM/F12 media supplemented with 10% FBS, glutamine and penicillin/streptomycin. After 48 h, 5 mM histidinol was added to the culture medium and viable clones were isolated and expanded. Their ability to differentiate into lipid filled cells was tested under differentiation conditions as described below. The clone presenting the highest lipid accumulation was grown until passage 8 and infected with a recombinant virus containing the HPV-E7 gene.

D. Differentiation of Chub-S7 Cells

Cells were grown in a mixture of DMEM/F12 media supplemented with 10% FBS, 2 mM glutamine, 100 U/ml penicillin/streptamycin until confluency. For differentiation, cells were washed with PBS and cultured with a serum-free medium consisting of a mixture of DMEM/F12 media supplemented with 15 mM NaHCO$_3$, 17 μM D-panthotenic acid, 15 mM Hepes, 33 μM biotin, 10 μg/ml transferrin, 1 nM triiodothyronin, 850 nM insulin and 500 μg/ml fetuin. This medium, referred to "basal medium" was supplemented with 1 μM dexamethasone (Dex) and 500 μM IBMX from day 0 to 3. Dex was maintained alone or with 1 μM BRL49653 from day 3 to 17 in order to promote differentiation. As stated in Results, oleic acid (OA) complexed with bovine serum albumin (BSA; ratio OA-to-BSA: 5: 1) was added to the medium containing BRL49653 from day 10 to 17. Lipid accumulation in differentiated cells was visualized by Oil red O staining as previously described (22). All the experiments on Chub-S7 cell characterization were performed between passages 18 and 32 (69 to 122 population doublings).

(iv) Glycerol-3-phosphate dehydrogenase activity and lipolysis measurements Glycerol-3-phosphate dehydrogenase (GPDH) activity measured at different times during the differentiation process of Chub-S7 cells was determined using the enzymatic assay previously described (23). Lipolysis was determined at day 17 after confluency. Cells were incubated 1 hour at 37° C. and 5% CO$_2$ with a Krebs-Ringer buffer (5 mM NaH$_2$PO$_4$; 1 mM MgSO$_4$; 1 mM CaCl$_2$; 136 mM NaCl; 4.7 mM KCl) supplemented with 20 mM Hepes, 2% BSA, 5 mM glucose and 1 μM isoproterenol as indicated in Results. Glycerol released in the medium was measured using the glycerokinase enzymatic radiometric assay described by Bradley and Kaslow (24).

E. Telomerase Repeat Amplification (TRAP) Assay

The TRAP protocol assay was performed on cell extracts as previously described (8)

F. Karyotype Analysis

Semi-confluent cultures were sent to the Cell Culture Laboratory (Children's Hospital of Michigan, Michigan, U.S.A.) for karyotyping analysis performed as previously described (8).

G. Analysis of Adipocyte Markers Expression

RNAs from Chub-S7 cells cultured from day 0 to 17 were extracted using the NucleoSpin® Total RNA Purification System (Macherey-Nagel, Oensingen Switzerland). Reverse transcription was performed with an input of 10 μg of total RNA using the 1$^{st}$ strand cDNA synthesis kit for RT-PCR (AMV; Roche Biomedical, Basel, Switzerland) with oligo d(T)$_{15}$ as primer. Real-time reverse transcription-polymerase chain reaction analyses were performed in a fluorescent temperature cycler (GeneAmp® PCR 5700 Sequence Detection System; Applied Biosystem) according to the recommendations of the manufacturer. Briefly, after initial denaturation at 50° C. for 2 min and 95° C. for 10 min, reactions were cycled 40 times using the following parameters for all genes studied: 95° C. for 15s, primer annealing and extension at 60° C. for 1 min. SYBR Green I fluorescence was detected at the end of each cycle to monitor the amount of PCR product formed during that cycle. Primers used for the amplification of cDNAs of interest were synthesized by Mycrosynth (Windisch, Switzerland).

The sequence of the forward and reverse primers are listed in Table 2 below. Cycle to cycle fluorescence emission was monitored and quantified using the GenAmp software provided by Applied Biosystem. Relative mRNA levels ($2^{\Delta Ct}$) were determined by comparing the PCR cycle threshold (Ct) between cells at day 0 and cells at days 6, 10, 13 and 17 after confluency (ΔCt). At day 0, all the genes studied had a detectable amplification level before the 40 cycles of the real-time PCR, with Ct values significantly lower than the Ct obtained in the absence of cDNA (not shown). The purity of the PCR products was checked by analyzing melting curves. The specificity of the amplification product was verified by performing a PCR under the conditions described above but during a number of cycle defined according to the linear amplification of the genes (number of cycles for the amplification of adipsin: 23; aP2: 20; C/EBPα: 25; Leptin: 29; LPL: 28; PPARγ; 23). The PCR products were subjected to electrophoresis on a 12% acrylamide gel followed by staining with Sybergold (Molecular probes, Leiden, The Netherlands).

TABLE 2

| | |
|---|---|
| Adipsin | Forward 5'-GCAACAAAGTCCCGAGCAA-3' (SEQ ID No. 21) reverse 5'-CCTTCTGCATATAGTAGGTGCTCAAT-3' (SEQ ID No. 22) |
| aP2 | forward 5'-AAACTGGTGGTGGAATGCG-3' (SEQ ID No. 23) reverse 5'-CCCTTGGCTTATGCTCTCTCA-3' (SEQ ID No. 24) |
| C/EBPα | forward 5'-ACTGGGACCCTCAGCCTTG-3' (SEQ ID No. 25) reverse 5'-TGGACTGATCGTGCTTCGTG-3' (SEQ ID No. 26) |
| Leptin | forward 5'-CCAGAAACGTGATCCAAATATCC-3' (SEQ ID No. 27) reverse 5'-GAAGGCCAGCACGTGAAGA-3' (SEQ ID No. 28) |

TABLE 2-continued

```
Lipoprotein Lipase (LPL)            forward 5'-TGCCCTAAGGACCCCTGAA-3'
                                    (SEQ ID No. 29)
                                    reverse 5'-CAGGTAGCCACGGACTCTGC-3'
                                    (SEQ ID No. 30)

Peroxysome proliferator acivated    forward 5'-CAAACACATCACCCCCCTG-3'
recceptor γ                         (SEQ ID No. 31)
(PPAR γ.)                           reverse 5'-AAACTGGCAGCCCTGAAAGA-3'
                                    (SEQ ID No. 32)

RPL p0                              forward 5'-CCACGCTGCTGAACATGCT-3'
                                    (SEQ ID No. 33)
                                    reverse 5'-TCGACACCTGCTGGATGAC-3'
                                    (SEQ ID No. 34)
```

H. Statistical Analysis

Statistical comparisons were performed on absolute values by ANOVA.

REFERENCES

1. Jha K K, Banga S, Palejwala V, Ozer H L. SV40-Mediated immortalization. Exp Cell Res 1998;245(1):1-7.
2. Shay J W, Wright W E, Werbin H. Defining the molecular mechanisms of human cell immortalization. Biochim Biophys Acta 1991;1072(1):1-7.
3. Huschtscha L I, Holliday R. Limited and unlimited growth of SV40-transformed cells from human diploid MRC-5 fibroblasts. J Cell Sci 1983;63:77-99.
4. Counter C M, Hahn W C, Wei W, Caddle S D, Beijersbergen R L, Lansdorp P M, et al. Dissociation among in vitro telomerase activity, telomere maintenance, and cellular immortalization. Proc Natl Acad Sci U.S.A. 1998; 95(25):14723-8.
5. Seigneurin-Venin S, Bernard V, Tremblay J P. Telomerase allows the immortalization of T antigen-positive DMD myoblasts: a new source of cells for gene transfer application. Gene Ther 2000;7(7):619-23.
6. Zhu J, Wang H, Bishop J M, Blackburn E H. Telomerase extends the lifespan of virus-transformed human cells without net telomere lengthening. Proc Natl Acad Sci U.S.A. 1999;96(7):3723-8.
7. Halvorsen T L, Leibowitz G, Levine F. Telomerase activity is sufficient to allow transformed cells to escape from crisis. Mol Cell Biol 1999; 19(3): 1864-70.
8. Darimont C, Avanti O, Tromvoukis Y, Vautravers-Leone P, Kurihara N, Roodman GD, et al. SV40 T antigen and telomerase are required to obtain immortalized human adult bone cells without loss of the differentiated phenotype. Cell Growth Differ 2002; 13(2):59-67.
9. Cherington V, Morgan B, Spiegelman B M, Roberts T M. Recombinant retroviruses that transduce individual polyoma tumor antigens: effects on growth and differentiation. Proc Natl Acad Sci U.S.A.1986;83(12):4307-11.
10. Cherington V, Brown M, Paucha E, St Louis J, Spiegelman B M, Roberts T M. Separation of simian virus 40 large-T-antigen-transforming and origin-binding functions from the ability to block differentiation. Mol Cell Biol 1988;8(3):1380-4.
11. Fajas L, Fruchart J C, Auwerx J. Transcriptional control of adipogenesis. Curr Opin Cell Biol 1998;10(2):165-73.
12. Takahashi N, Kawada T, Yamamoto T, Goto T, Taimatsu A, Aoki N, et al. Overexpression and ribozyme-mediated targeting of transcriptional coactivators CREB-binding protein and p300 revealed their indispensable roles in adipocyte differentiation through the regulation of peroxisome proliferator-activated receptor gamma. J Biol Chem 2002;277(19):16906-12.
13. Erickson R L, Hemati N, Ross S E, MacDougald O A. p300 coactivates the adipogenic transcription factor CCAAT/enhancer-binding protein alpha. J Biol Chem 2001;276(19): 16348-55.
14. Cho S, Tian Y, Benjamin T L. Binding of p300/CBP co-activators by polyoma large T antigen. J Biol Chem 2001;276(36):33533-9.
15. Lill N L, Grossman S R, Ginsberg D, DeCaprio J, Livingston D M. Binding and modulation of p53 by p300/CBP coactivators. Nature 1997;387(6635):823-7.
16. Forest C, Czerucka D, Negrel R, Ailhaud G. Establishment of a human cell line after transformation by a plasmid containing the early region of the SV40 genome. Cell Biol Int Rep 1983;7(1):73-81.
17. Zwerschke W, Jansen-Durr P. Cell transformation by the E7 oncoprotein of human papillomavirus type 16: interactions with nuclear and cytoplasmic target proteins. Adv Cancer Res 2000;78:1-29.
18. Huang S M, McCance D J. Down regulation of the interleukin-8 promoter by human papillomavirus type 16 E6 and E7 through effects on CREB binding protein/p300 and P/CAF. J Virol 2002;76(17):8710-21.
19. Coursen J D, Bennett W P, Gollahon L, Shay J W, Harris C C. Genomic instability and telomerase activity in human bronchial epithelial cells during immortalization by human papillomavirus-16 E6 and E7 genes. Exp Cell Res 1997;235(1):245-53.
20. Pfeifer A M A, Mace K, Tromvoukis Y, Lipsky M M. Highly efficient establishment of immortalized cells from adult human liver. Meth. Cell Science 1995;17:83-89.
21. Sugihara H, Yonemitsu N, Miyabara S, Yun K. Primary cultures of unilocular fat cells: characteristics of growth in vitro and changes in differentiation properties. Differentiation 1986;31 (1):42-9.
22. Ramirez-Zacarias J L, Castro-Munozledo F, Kuri-Harcuch W. Quantitation of adipose conversion and triglycerides by staining intracytoplasmic lipids with Oil red O. Histochemistry 1992;97(6):493-7.
23. Sottile V, Seuwen K. Bone morphogenetic protein-2 stimulates adipogenic differentiation of mesenchymal precursor cells in synergy with BRL 49653 (rosiglitazone). FEBS Lett 2000;475(3):201-4.
24. Bradley D C, Kaslow H R. Radiometric assays for glycerol, glucose, and glycogen. Anal Biochem 1989;180 (1):11-6.

What is claimed is:

1. An isolated culture of an immortalized human pre-adipose cell line, wherein the immortalized human pre-adipose cell are genetically engineered to express a human papillomavirus E7 oncoprotein and a telomerase reverse transcriptase gene, wherein the immortalized human pre-adipose cell is capable of maturing into an immortalized mature white adipose cell, wherein the mature adipose cell exhibits a metabolic pattern of normal human white adipose cells when cultured on serum-free medium, wherein the adipose cell expresses at least four normal human white adipose cell markers selected from the group consisting of: lipoprotein lipase; fatty acid synthase; adipocyte fatty acid binding protein; leptin; adipsin; ad iponectin; peroxisome proliferator-activated receptors γ; peroxisome proliferator-activated receptors β; CCAAT/enhancer binding protein alpha; and hormone sensitive lipase.

2. The culture of claim 1, wherein the immortalized white adipose cell expresses lipoprotein lipase; leptin; adiponectin; and peroxisome proliferator-activated receptors γ.

3. The culture of claim 2, wherein the immortalized white adipose cell expresses CCAAT/enhancer binding protein alpha, adipocyte fatty acid binding protein or adipsin.

4. The culture of claim 1, wherein the immortalized white adipose cell has a karyotype identical to a normal white adipose cell.

5. The culture of claim 1, wherein the immortalized human pre-adipose cell is CNCM I-2520 or CNCM I-2663.

6. An isolated immortalized mature adipose cell comprising a mature adipose cell derived from the culture of claim 1.

7. The adipose cell of claim 6, wherein the adipose cell can be kept in culture for at least 20 passages.

8. The adipose cell of claim 6, wherein the adipose cell is derived from the adipose cell line CNCM I-2520 or CNCM I-2663.

9. A method for preparing an isolated pre-adipose cell line according to claim 1 which comprises the steps:
   (a) separating cells from a human adipose tissue;
   (b) de-differentiating the cells obtained in (a) into fibroblast-like cells deprived of liquid droplets and proliferating the-said cells obtained in (a) to obtain a pre-adipose cell clone;
   (c) immortalizing the pre-adipose cell clone isolated under step (b) by transfecting the clone with an expression vector encoding a human papillomavirus E7 oncoprotein and a telomerase reverse transcriptase gene;
   (d) selecting for immortalized cells, and
   (e) selecting for cells capable of differentiating into white adipose cells.

10. The method according to claim 9, wherein the adipose cell line produced has the identifying characteristics of CNCM I-2520 or CNCM I-2663.

11. An isolated human pre-adipose cell line comprising a cell line selected from the group consisting of CNCM I-2520 and CNCM I-2663.

12. The method according to claim 9, wherein the immortalization step includes successively transfecting the clone with an expression vector encoding the human papillomavirus E7 oncoprotein and the telomerase reverse transcriptase gene.

* * * * *

SEQUENCE LISTING

<160> NUMBER OF SEQ ID NOS: 34

<210> SEQ ID NO 1
<211> LENGTH: 20
<212> TYPE: DNA
<213> ORGANISM: homo sapien
<220> FEATURE:
<223> OTHER INFORMATION: DNA

<400> SEQUENCE: 1
ggattcagtg gtgtatgact 20

<210> SEQ ID NO 2
<211> LENGTH: 20
<212> TYPE: DNA
<213> ORGANISM: homo sapien
<220> FEATURE:
<223> OTHER INFORMATION: DNA

<400> SEQUENCE: 2
aggcacactg tactcattca 20

<210> SEQ ID NO 3
<211> LENGTH: 20
<212> TYPE: DNA
<213> ORGANISM: homo sapien
<220> FEATURE:
<223> OTHER INFORMATION: DNA

<400> SEQUENCE: 3
ggagatacac ctacattgca 20

<210> SEQ ID NO 4
<211> LENGTH: 20
<212> TYPE: DNA
<213> ORGANISM: homo sapien
<220> FEATURE:
<223> OTHER INFORMATION: DNA

<400> SEQUENCE: 4
gatggggcac acaattccta 20

<210> SEQ ID NO 5
<211> LENGTH: 18
<212> TYPE: DNA
<213> ORGANISM: homo sapien
<220> FEATURE:
<223> OTHER INFORMATION: DNA

<400> SEQUENCE: 5
gttgctatcc aggctgtg 18

<210> SEQ ID NO 6
<211> LENGTH: 18
<212> TYPE: DNA
<213> ORGANISM: homo sapien
<220> FEATURE:
<223> OTHER INFORMATION: DNA

<400> SEQUENCE: 6
catagtccgc ctagaagc 18

<210> SEQ ID NO 7
<211> LENGTH: 18

```
<212> TYPE: DNA
<213> ORGANISM: homo sapien
<220> FEATURE:
<223> OTHER INFORMATION: DNA

<400> SEQUENCE: 7
tacagctgtc ggagaagg                                                 18

<210> SEQ ID NO 8
<211> LENGTH: 20
<212> TYPE: DNA
<213> ORGANISM: homo sapien
<220> FEATURE:
<223> OTHER INFORMATION: DNA

<400> SEQUENCE: 8
ttcttgcggt tgccgcaaac                                               20

<210> SEQ ID NO 9
<211> LENGTH: 20
<212> TYPE: DNA
<213> ORGANISM: homo sapien
<220> FEATURE:
<223> OTHER INFORMATION: DNA

<400> SEQUENCE: 9
gggagctgtt ctactgctat                                               20

<210> SEQ ID NO 10
<211> LENGTH: 20
<212> TYPE: DNA
<213> ORGANISM: homo sapien
<220> FEATURE:
<223> OTHER INFORMATION: DNA

<400> SEQUENCE: 10
ctccaatccc acactgaatg                                               20

<210> SEQ ID NO 11
<211> LENGTH: 20
<212> TYPE: DNA
<213> ORGANISM: homo sapien
<220> FEATURE:
<223> OTHER INFORMATION: DNA

<400> SEQUENCE: 11
ggtacctgga aacttgtctc                                               20

<210> SEQ ID NO 12
<211> LENGTH: 20
<212> TYPE: DNA
<213> ORGANISM: homo sapien
<220> FEATURE:
<223> OTHER INFORMATION: DNA

<400> SEQUENCE: 12
aacttcagtc caggtcaacg                                               20

<210> SEQ ID NO 13
<211> LENGTH: 20
<212> TYPE: DNA
<213> ORGANISM: homo sapien
<220> FEATURE:
<223> OTHER INFORMATION: DNA

<400> SEQUENCE: 13
```

-continued

| | |
|---|---|
| tttctctgta tggcaccgtg | 20 |

<210> SEQ ID NO 14
<211> LENGTH: 20
<212> TYPE: DNA
<213> ORGANISM: homo sapien
<220> FEATURE:
<223> OTHER INFORMATION: DNA

<400> SEQUENCE: 14

| | |
|---|---|
| ttcacaaata ccgcaggtgc | 20 |

<210> SEQ ID NO 15
<211> LENGTH: 20
<212> TYPE: DNA
<213> ORGANISM: homo sapien
<220> FEATURE:
<223> OTHER INFORMATION: DNA

<400> SEQUENCE: 15

| | |
|---|---|
| ggtcttgaga gatggcttgc | 20 |

<210> SEQ ID NO 16
<211> LENGTH: 20
<212> TYPE: DNA
<213> ORGANISM: homo sapien
<220> FEATURE:
<223> OTHER INFORMATION: DNA

<400> SEQUENCE: 16

| | |
|---|---|
| caggttgaca gcagccaagt | 20 |

<210> SEQ ID NO 17
<211> LENGTH: 20
<212> TYPE: DNA
<213> ORGANISM: homo sapien
<220> FEATURE:
<223> OTHER INFORMATION: DNA

<400> SEQUENCE: 17

| | |
|---|---|
| tcaacgacca ggttaccctt | 20 |

<210> SEQ ID NO 18
<211> LENGTH: 20
<212> TYPE: DNA
<213> ORGANISM: homo sapien
<220> FEATURE:
<223> OTHER INFORMATION: DNA

<400> SEQUENCE: 18

| | |
|---|---|
| cttgatccgc tgcatcatct | 20 |

<210> SEQ ID NO 19
<211> LENGTH: 20
<212> TYPE: DNA
<213> ORGANISM: homo sapien
<220> FEATURE:
<223> OTHER INFORMATION: DNA

<400> SEQUENCE: 19

| | |
|---|---|
| gtgcaggaga tcacagagat | 20 |

<210> SEQ ID NO 20
<211> LENGTH: 20
<212> TYPE: DNA
<213> ORGANISM: homo sapien

```
<220> FEATURE:
<223> OTHER INFORMATION: DNA

<400> SEQUENCE: 20
ttgccaagtc gctgtcatct                                              20

<210> SEQ ID NO 21
<211> LENGTH: 19
<212> TYPE: DNA
<213> ORGANISM: homo sapien
<220> FEATURE:
<223> OTHER INFORMATION: DNA

<400> SEQUENCE: 21
gcaacaaagt cccgagcaa                                               19

<210> SEQ ID NO 22
<211> LENGTH: 26
<212> TYPE: DNA
<213> ORGANISM: homo sapien
<220> FEATURE:
<223> OTHER INFORMATION: DNA

<400> SEQUENCE: 22
ccttctgcat atagtaggtg ctcaat                                       26

<210> SEQ ID NO 23
<211> LENGTH: 19
<212> TYPE: DNA
<213> ORGANISM: homo sapien
<220> FEATURE:
<223> OTHER INFORMATION: DNA

<400> SEQUENCE: 23
aaactggtgg tggaatgcg                                               19

<210> SEQ ID NO 24
<211> LENGTH: 21
<212> TYPE: DNA
<213> ORGANISM: homo sapien
<220> FEATURE:
<223> OTHER INFORMATION: DNA

<400> SEQUENCE: 24
cccttggctt atgctctctc a                                            21

<210> SEQ ID NO 25
<211> LENGTH: 19
<212> TYPE: DNA
<213> ORGANISM: homo sapien
<220> FEATURE:
<223> OTHER INFORMATION: DNA

<400> SEQUENCE: 25
actgggaccc tcagccttg                                               19

<210> SEQ ID NO 26
<211> LENGTH: 20
<212> TYPE: DNA
<213> ORGANISM: homo sapien
<220> FEATURE:
<223> OTHER INFORMATION: DNA

<400> SEQUENCE: 26
tggactgatc gtgcttcgtg                                              20
```

<210> SEQ ID NO 27
<211> LENGTH: 23
<212> TYPE: DNA
<213> ORGANISM: homo sapien
<220> FEATURE:
<223> OTHER INFORMATION: DNA

<400> SEQUENCE: 27
ccagaaacgt gatccaaata tcc                              23

<210> SEQ ID NO 28
<211> LENGTH: 19
<212> TYPE: DNA
<213> ORGANISM: homo sapien
<220> FEATURE:
<223> OTHER INFORMATION: DNA

<400> SEQUENCE: 28
gaaggccagc acgtgaaga                                   19

<210> SEQ ID NO 29
<211> LENGTH: 19
<212> TYPE: DNA
<213> ORGANISM: homo sapien
<220> FEATURE:
<223> OTHER INFORMATION: DNA

<400> SEQUENCE: 29
tgccctaagg acccctgaa                                   19

<210> SEQ ID NO 30
<211> LENGTH: 20
<212> TYPE: DNA
<213> ORGANISM: homo sapien
<220> FEATURE:
<223> OTHER INFORMATION: DNA

<400> SEQUENCE: 30
caggtagcca cggactctgc                                  20

<210> SEQ ID NO 31
<211> LENGTH: 19
<212> TYPE: DNA
<213> ORGANISM: homo sapien
<220> FEATURE:
<223> OTHER INFORMATION: DNA

<400> SEQUENCE: 31
caaacacatc acccccctg                                   19

<210> SEQ ID NO 32
<211> LENGTH: 20
<212> TYPE: DNA
<213> ORGANISM: homo sapien
<220> FEATURE:
<223> OTHER INFORMATION: DNA

<400> SEQUENCE: 32
aaactggcag ccctgaaaga                                  20

<210> SEQ ID NO 33
<211> LENGTH: 19
<212> TYPE: DNA
<213> ORGANISM: homo sapien
<220> FEATURE:
<223> OTHER INFORMATION: DNA

```
<400> SEQUENCE: 33
ccacgctgct gaacatgct                                              19

<210> SEQ ID NO 34
<211> LENGTH: 20
<212> TYPE: DNA
<213> ORGANISM: homo sapien
<220> FEATURE:
<223> OTHER INFORMATION: DNA

<400> SEQUENCE: 34
tcgaacacct gctggatgac                                             20
```